US008133683B2

(12) United States Patent
Wu et al.

(10) Patent No.: US 8,133,683 B2
(45) Date of Patent: Mar. 13, 2012

(54) METHODS FOR DETECTING BIOMOLECULES IN A SAMPLE

(75) Inventors: Yu-Wei Wu, Taipei (TW); Yu-Hui Tsai, Taipei (TW)

(73) Assignee: Taipei Medical University, Taipei (TW)

( * ) Notice: Subject to any disclaimer, the term of this patent is extended or adjusted under 35 U.S.C. 154(b) by 0 days.

(21) Appl. No.: 12/358,884

(22) Filed: Jan. 23, 2009

(65) Prior Publication Data
US 2010/0190189 A1 Jul. 29, 2010

(51) Int. Cl.
*G01N 33/53* (2006.01)
(52) U.S. Cl. .......................................... 435/7.1
(58) Field of Classification Search .................. None
See application file for complete search history.

(56) References Cited

U.S. PATENT DOCUMENTS

| | | | | |
|---|---|---|---|---|
| 3,981,983 | A * | 9/1976 | Caston et al. ................. | 435/7.8 |
| 4,081,402 | A * | 3/1978 | Levy et al. .................... | 428/36.4 |
| 5,656,207 | A * | 8/1997 | Woodhead et al. ............ | 252/700 |
| 5,962,221 | A * | 10/1999 | Caetano-Anolles ......... | 435/6.12 |
| 6,979,424 | B2 * | 12/2005 | Northrup et al. ................ | 422/50 |
| 2005/0208510 | A1 * | 9/2005 | Latham et al. .................... | 435/6 |
| 2006/0246475 | A1 * | 11/2006 | Peterson et al. .................. | 435/6 |
| 2009/0021728 | A1 * | 1/2009 | Heinz et al. .................... | 356/244 |

OTHER PUBLICATIONS

J Biomol Screen 2006 11: 836, "A Rapid Transglutaminase Assay for High-Throughput Screening Applications", Wu et al.*
Petrenko, V. A. and Vodyanoy, V. J.,(2003) Phage display for detection of biological threat agents, J. Microbiol. Methods 53, 253-262, Journal.
Andresen, H., Grotzinger, C., Zarse, K., Kreuzer, O. J., Ehrentreich-Forster, E., and Bier, F. F., (2006) Functional peptide microarrays for specific and sensitive antibody diagnostics, Proteomics. 6, 1376-1384, Journal.
Al-Dujaili, E. A. S., Forrest, G. C., Edwards, C. R.W., and Landon J., (1979) Clin.l Chem. 25, 1402-1405, Journal.
Tan, W. S., Tan, G. H., Yusoff, K., and Seow, H. F., (2005) A phage-displayed cyclic peptide that interacts tightly with the immunodominant region of hepatitis B surface antigen, J. Clin. Virol. 34, 35-41, Journal.
Lu, X., Weiss, P., and Block, T., (2004) A phage with high affinity for hepatitis B surface antigen for the detection of HBsAg, J. Virol. Methods 119, 51-54, Journal.
Freifelder DM: Immunological Methods. In Freifelder DM, (ed): Physical Biochemistry: Applications to Biochemistry and Molecular Biology. 2nd ed. San Francisco: Freeman, 1982:323-360. p. 335,336, Journal.
Wu, Y. W. and Tsai, Y. H., (2006) A rapid transglutaminase assay for high-throughput screening applications, J. Biomol. Screen. 11, 836-843, Journal.
Bessette, P. H., Rice, J. J., and Daugherty, P.S., (2004) Rapid isolation of high-affinity protein-binding peptides using bacterial display, Protein Engineering, Design & Selection 17, 731-739, Journal.
Dennis, M. S., Zhang, M., Meng, Y. G., Kadkhodayan, M., Kirchhofer, D., Kombs, D., and Damico, L. A., (2002) Albumin binding as a general strategy for improving the pharmacokinetics of proteins, The Journal of Biological Chemistry 277, 35035-35043, Journal.

* cited by examiner

*Primary Examiner* — Ann Y Lam
(74) *Attorney, Agent, or Firm* — WPAT, P.C.; Anthony King (57) ABSTRACT

The invention develops a high-throughput screening method based on charcoal-sorbent peptide binding assay (CPBA) which does not need a solid phase and can simultaneously detect plural target biomolecules in a sample. The method of the invention can achieve high-throughput screening of biomolecules (such as antibodies and antigens) with a molecular weight of more than 10 KD.

10 Claims, 5 Drawing Sheets

METHODS FOR DETECTING BIOMOLECULES IN A SAMPLE

FIELD OF THE INVENTION

The invention relates to a high-throughput screening method based on charcoal-sorbent peptide binding assay (CPBA). In particular, the invention provides a method for simultaneously screening a number of biomolecules in a sample.

BACKGROUND OF THE INVENTION

The detection of a ligand by a receptor (for example, detection of an hormone, an antigen or a pathogenic agent by an antibody, detection of an antibody in blood by another antibody, or binding of a chemical toxin) is important in the diagnosis of diseases and finding of useful biomolecules. Many rapid test methods for detecting ligands with high selectivity and sensitivity have been developed in the past years. These include radio-activity based immunoassay, chemiluminescence based immunoassay, magnetic based assay, fluorescence or colorimetric analysis based immunoassay. Immunoassays, such as enzyme-linked immunosorbent assay (ELISA), enzyme immunoassay (EIA), and radioimmunoassay (RIA), are well known for the detection of ligands such as hormones, antigens or antibodies. The basic principle in many of these assays is that a marker-conjugated (for example, an enzyme-, chromogen-, fluorogen-, or radio-nucleotide-conjugated) antibody permits antigen detection upon antibody binding. In order for this interaction to be detected as a change in color, fluorescent or radioactive complexes, significant numbers of antibodies must be bound to a correspondingly large number of antigen epitopes. The resulting labeled binding complex must be isolated from the labeled marker molecules for detection. Currently, the isolation methods include ammonium sulfate or antibody precipitation, chromatography, solid phase assay, dialysis and active carbon adsorption.

The heterogeneous immunoassay usually includes the isolation procedure to separate the free analytes (or antibodies) from the bound immunocomplexes. Traditionally, the method for immunocomplex isolation includes fractionation precipitation, immunoprecipitation, column chromatography, solid-phase analysis, dialysis, and the absorption of dextran-coated charcoal. Fractionation precipitation uses the salts or organic solvents to fractionally precipitate target proteins. Immunoprecipitation uses antibodies in complex with the target antigens or antibodies to form the insoluble immunocomplex which is further precipitated by centrifugation. Column chromatography uses chromatographic method to sequentially separate analytes and enriches the immunocomplex in the collection tube. In solid-phase immunoassay, ligands are coated on a plate or a bead before interacting with the receptors. Dialysis can separate the unbound small molecules from the large immunocomplexes by using a molecular sieving membrane. All the methods mentioned above have various disadvantages such as having a complex procedure, or being time-consuming and expensive, which limit the application for high throughput assay. Separation of free analytes from large immunocomplexes can also be achieved by using the dextran-coated charcoal, but the traditional use of dextran-coated charcoal in immunoassay is for diagnosis of small molecules (e.g., steroid hormone or insulin) in serum (Clinical Chemistry 25 (1979) 1402-1405). So far, dextran-coated charcoal has not been able to apply to the analysis of large antigens, or antibodies that are specific for large antigens, and this should be further improved.

The essential element of any immuno-based detection is the probe that binds analyte and, as a part of the analytical platform, generates a measurable signal. Peptide probes that specifically bind to biomolecules are developed as probes to detect analytes. Such peptide probes can be selected by using various methods. For example, a peptide that is an epitope or a mimotope fragment of a pathogenic antigen can be used to screen the infected antiserum. In addition, a peptide that specifically interacts with an antigen or an antibody can be screened by using phage display technique or similar screening methods. Peternko and Vodyanoy summarizes the state of art in development of the probes for detection of biological threat agents and focuses on phage display, which is new in the detection area and specializes in development of molecular probes to target various biological structures (Journal of Microbiological Methods 53 (2003) 253-262). Dennis et al. describes the phage displayed peptide (DICLPRWGCLW) that can specifically interact with serum albumin (The Journal of Biological Chemistry 277(38) (2002) 35035-35043). Bessette et al. screens specific binding peptides for human serum albumin, anti-T7 epitope mAb, human C-reactive protein, HIV-1 GP120 and streptavidin by using bacterial display technique (Protein Engineering, Design & Selection 17(10) (2004) 731-739). Lu et al. (Journal of Virological Methods 119 (2004) 51-54) and Tan et al. (Journal of Clinical Virology 34 (2005) 35-41) develop the phage bearing peptides that interact tightly with the immunodominant region of hepatitis B surface antigen (HBsAg), and demonstrate the ELISA-like methods for HBsAg detection by using these peptides. The above disclosure indicates that the specific peptides have the potential to be used as diagnostic agents.

Some rapid test systems incorporate more than one immunology-based technique into the system to improve specificity and/or sensitivity. Immunology-based rapid assays already in existence can be further modified or incorporated into other systems to improve their performance, which obviates the need to create entirely new detection systems. Array based immunoassay techniques for multi-analyte detection produce high-density arrays formed by spatially addressable synthesis of bioactive probes on a 2-dimensional solid support and have greatly enhanced and simplified the process of biological research and development. Proteomics 2006, 6, 1376-1384 discloses a method for manufacturing peptide microarrays for molecular immune diagnostics. However, these array systems utilize immunology-based assay, so they still have the disadvantages mentioned above.

Wu and Tsai (Journal of Biomolecular Screening 11 (7) (2006) 836-843) discloses a rapid transglutaminase assay for high-throughput screening applications on the basis of magnetic dextran-coated charcoal. This article only mentions the screening of transglutaminase activity by detecting the conjugation of casein and dansylcadaverine, but does not teach the concept of antibody or antigen detection by using a specific peptide probe.

Accordingly, there remains a need for a high-throughput screening method for simultaneously detecting more than one target biomolecule in a sample.

SUMMARY OF THE INVENTION

The invention provides a high-throughput screening method for detecting one or more target biomolecules in a sample, which comprises the steps of:
(a) mixing one or more marker-labeled peptide probes with a specimen that contains one or more target biomolecules of respective probe, each peptide probe only specifically binding to its target biomolecule;
(b) adding dextran-coated charcoal to the reaction mixture to capture all the unbound peptide probes;
(c) precipitating the dextran-coated charcoal through centrifugation or magnetic sedimentation so that the biomolecule-bound and -unbound peptide probes are separated; and
(d) collecting the biomolecule-bound peptide probe complexes and detecting the signals of the markers with respective detection parameters.

BRIEF DESCRIPTION OF THE DRAWING

FIG. 1A is the basic principle of the assay. The combination of specific antibodies with peptide probes is initiated by mixing serum samples with the synthesized, labeled, epitope- (or mimotope-) based peptides. After incubation, the unbound peptides are rapidly removed from the immune complex by magnetic dextran-coated charcoal (MD-Charcoal) treatment. MD-Charcoal is then magnetically precipitated. The signal of the binding complex remaining in the supernatant is now ready to be measured. FIG. 1B is a basic protocol of the assay. Serum samples (30 μl/well) are separately placed in the wells of a microplate at 4° C. (Step 1). Upon the addition of the specific peptide probes (30 μl/well) (Step 2), the binding reaction is initiated by incubating the plate at 37° C. for an indicated period of time (Step 3), and terminated by adding 200 μl MD-Charcoal (Step 4). The plate is kept at room temperature for 5 minutes to remove all of the unbound peptides (Step 5). Finally, the MD-Charcoal is precipitated by magnet (Step 6), and the signal of the binding complex in the supernatant is then measured (Step 7). It should be noted that in Step 6, if the peptide probes are labeled with fluorescent dyes, the transfer of the supernatant to another plate for fluorescence measurement is not necessary because the precipitated MD-Charcoal captured probes do not exhibit fluorescent properties; otherwise, the supernatants are collected in the respective well of another microplate for counting.

FIG. 2A confirms the production of anti-KY15 antiserum by using ELISA. Microplate wells coated with peptide KY15 or skim milk (control) were used to demonstrate the specification of anti-KY15 antiserum. FIG. 2B shows the specific binding of FITC-KY15 with anti-KY15 antibody as analyzed by using CPBA method. The control sera, anti-FF15 antiserum and non-immune rabbit serum did not show affinity for the peptide probe, FITC-KY15. The experiment is described in detail in Example 1. Each datum point represents means±SD (n=3).

FIG. 3A is the basic principle of the assay. The interaction of specific antigens with peptide probes is initiated by mixing serum samples with the synthesized, labeled peptide probes at 37° C. After incubation, the unbound peptides are rapidly removed from the antigen-peptide complex by magnetic dextran-coated charcoal (MD-Charcoal) treatment. MD-Charcoal is then magnetically precipitated. The signal of the antigen-peptide complex remaining in the supernatant is now ready to be measured. FIG. 3B is a basic protocol of the assay. Serum samples (30 μl/well) are placed separately in the wells of a microplate at 4° C. (Step 1). Upon the addition of the specific peptide probes (30 μl/well) (Step 2), the binding reaction is initiated by incubating the plate at 37° C. for an indicated period of time (Step 3), and terminated by adding 200 μl MD-Charcoal (Step 4). The plate is kept at room temperature for 5 minutes to remove all of the unbound peptides (Step 5). Finally, the MD-Charcoal is precipitated by magnet (Step 6), and the signal of the antigen-peptide complex in the supernatant is measured (Step 7). It should be noted that in Step 6, if the peptide probes are labeled with fluorescent dyes, the transfer of the supernatant to another plate for fluorescence measurement is unnecessary because the precipitated MD-Charcoal does not exhibit fluorescent properties; otherwise, the supernatants are collected in another microplate for counting.

FIG. 4 illustrates the specific detection of human serum albumin (HSA). The albumin-specific peptide probe, FITC-RD18, was used for HSA detection. The specific binding of FITC-RD18 with HSA was linearly dose-dependent. Peptide FITC-KY15 was also applied as a negative control. Proteins such as ovalbumin (Ovalb) or bovine gamma globulin (BGG) did not interact with FITC-RD18. The experiment is described in detail in Example 2. Each datum point represents means±SD (n=3).

FIG. 5 illustrates the binding assay for multiple antibodies and antigens within one specimen. The binding of antibodies and antigens with their corresponding specific peptide probes are initiated by mixing serum samples with the variously labeled synthetic peptide probes. After incubation, the unbound peptide probes are rapidly removed from the binding complex by magnetic dextran-coated charcoal (MD-Charcoal) treatment. MD-Charcoal is then magnetically precipitated. The signals of the various labeled materials remaining in the supernatant are now ready for measurement at designated excitation/emission wavelength accordingly.

DETAILED DESCRIPTION OF THE INVENTION

The invention develops a high-throughput screening method based on charcoal-sorbent peptide binding assay (CPBA) which does not need a solid phase and can simultaneously detect plural target biomolecules in a sample. The method of the invention can achieve high-throughput screening of biomolecules (such as antibodies and antigens) without limitation on the molecular weight of the biomolecules.

The invention provides a high-throughput method, for detecting one or more target biomolecules in a sample, which comprises the steps of:
(a) mixing one or more marker-labeled peptide probes with a specimen that contains one or more target biomolecules of respective probe, each peptide probe only specifically binding to its target biomolecule;
(b) adding dextran-coated charcoal to the reaction mixture to capture all of the unbound peptide probes;
(c) precipitating the dextran-coated charcoal by centrifugation or magnetic sedimentation so that the biomolecule-bound and -unbound peptide probes are separated; and
(d) collecting the biomolecule-bound peptide probe complexes and detecting the signals of the markers with respective detection parameters.

As used herein, the word "comprise", or variations such as "comprises" or "comprising", will be understood to imply the inclusion of a stated element or group of elements, but not to the exclusion of any other element or group of elements.

As used herein, a "peptide" is an oligomer in which the monomers are amino acids and which is joined with another peptide through amide bonds, and is alternatively referred to as a polypeptide. Peptides are constituted with at least two amino acids, and are usually, but not exclusively, less than 50 amino acids in length. Peptides are small molecules that can be adsorbed by dextran-coated charcoal. For optimal adsorption of peptides by dextran-coated charcoal in this invention, the molecular weight of the peptides is less than 10 KD.

According to the invention, the peptide probes described herein may be partially or fully synthetic, and may, for example, comprise one or more of the following moieties: cyclized residues or peptides, multimers of peptides, labels, and/or other chemical moieties. The peptide probes of the invention described herein may interact with, but are not limited to, antibodies, or antigens such as specific proteins, nucleic acids, lipids, or polysaccharides. The peptide probes are generally specific for the target biomolecule to be detected. For example, peptides RLIEDICLPRWG-CLWEDD and WVCTWNYWTRVTWCL can specifically bind albumin and CP120 protein of HIV-1, respectively; peptides TKTFTVTE and CGETGAKPHC can specifically bind HBsAg. These peptides can be used as probes for antigens detection when the use of specific antibodies is not necessary.

According to the invention, the peptide probes are labeled with a detectable marker directly or indirectly, so that the peptide probe-biomolecule complex can be detected. According to the invention, the marker includes, but is not limited to, a fluorophore (e.g., FITC, TRITC, rhodamine), a radioisotope (e.g., $^3$H, $^{32}$P, $^{35}$S, $^{14}$C or $^{125}$I), or a micro-enzyme (e.g., microperoxidase, MW=2 KD). According to the invention, a specific biomolecule in a specimen can be quantified by counting the signals of the marker directly or indirectly. When the labeled marker is a fluorophore or radioisotope, the presence of the biomolecule can be quantified directly by counting the signal of the marker; when the labeled marker is a microperoxidase, it is quantified indirectly by measuring the catalytic activity of the microperoxidase.

As used herein, a "target biomolecule" is any molecule that can be specifically targeted with a peptide probe to form the conjugated product. Such biomolecules include, but are not limited to, antibodies, or antigens such as specific proteins, nucleic acids, lipids, or polysaccharides. However, the biomolecule must have molecular weight more than 10 KD so that it cannot be adsorbed by dextran-coated charcoal.

According to the invention, the method of the invention can be used to detect any target biomolecule with suitable peptide probes. Furthermore, the method of the invention can use one or more peptide probes to screen one or more biomolecules that have affinity to the peptide probes in a sample. According to one preferred embodiment of the invention, the method of the invention can simultaneously screen more than one biomolecule in a sample by using peptide probes labeled with various markers. According to the invention, the peptide probe binds to the biomolecule to form conjugated product.

As used herein, "dextran-coated charcoal" is commercially available or prepared by a method known in the art. For example, the dextran-coated charcoal is prepared by incubating activated charcoal with dextran in phosphate buffer. The dextran-charcoal complex is further purified by centrifugation and re-suspend in distilled water. Alternatively, the dextran-coated charcoal can be obtained from commercial source such as Bangs Laboratories, Inc. (Fishers, Ind.). (BioMag® Dextran-coated Charcoal). The "magnetic dextran-coated charcoal" used in the invention is dextran-coated charcoal coupled with a magnetic material that is commercially available (such as BioMag® magnetic dextran-coated charcoal from Bangs Laboratories, Inc., Fishers, Ind.). It is known that dextran-coated charcoal can work as a molecular sieve to absorb small molecules exclusively and virtually instantaneously (Physical Biochemistry: Applications to Biochemistry and Molecular Biology. $2^{nd}$ ed. San Francisco. Freeman, 1982: pp 323-360).

According to the invention, the dextran-coated charcoal or magnetic dextran-coated charcoal is used for rapid separation of the bound peptide probes from the unbound peptide probes. Since the peptide probe of the invention has low molecular weight, it can be adsorbed by the dextran-coated charcoal or magnetic dextran-coated charcoal, whereas the peptide probe conjugated with the target biomolecule has high molecular weight and thus cannot be adsorbed by the magnetic dextran-coated charcoal. The peptide probes conjugated with specific biomolecules are separated from dextran-coated charcoal by centrifugation. Alternatively, this separation step can be rapidly achieved by using magnet precipitation if magnetic dextran-coated charcoal is used.

The binding of peptide probes with specific biomolecules and the use of dextran-coated charcoal can be combined as an article of manufacture, for example, as a kit. Chemical agents within a kit can be housed together in various combinations or can be packaged in separate vials or containers. Articles in a kit can also include labels and/or packaging inserts setting out instructions for preparation and use.

The method of the invention is rapid, highly sensitive and inexpensive and no solid phase is necessary to practice this method. In particular, the method of the invention can simultaneously screen a number of biomolecules in a sample and can be easily carried out in a microplate. Therefore, the method of the invention and the kit using the method can replace and advance immunoassay for high-throughput screening of a number of biomolecules at the same time.

EXAMPLE

Example 1

Method for Detecting a Specific Antibody

Figure 1:
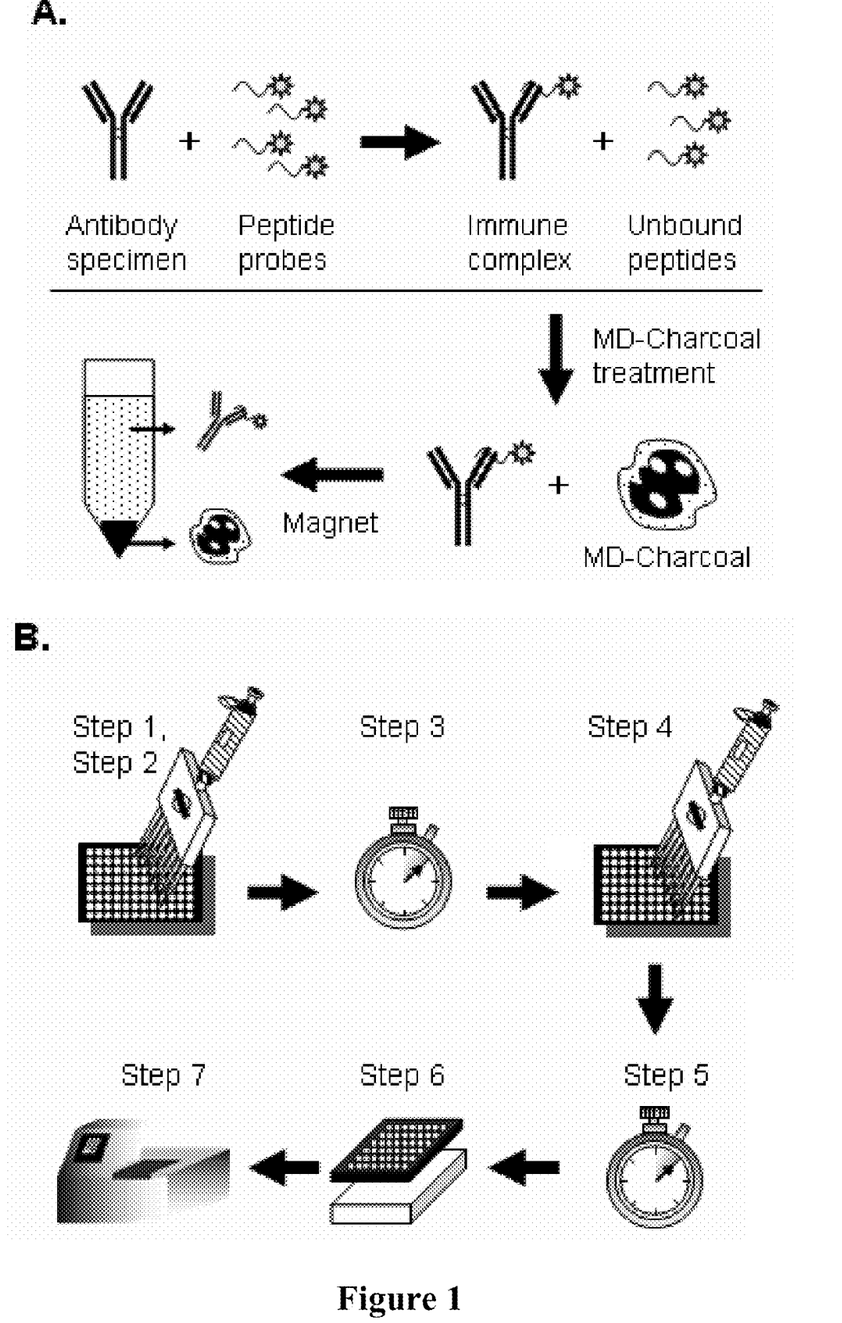
FIG. 1 illustrates the schemes of the antibody-detection method.

The protocol of the antibody detection method is illustrated in FIG. 1. To confirm that the method was practicable, peptide KY15 was synthesized and served as an epitope peptide of a particular protein. Anti-KY15 antiserum was produced through immunization of rabbits with peptide KY15. FITC-labeled KY15 was synthesized as the peptide probe for anti-KY15 antibody detection.

Materials

Rabbits were from the Animal Center of National Taiwan University. Peptides KY15 and FF15 (amino acid sequences: KSVGRDEREDITYTY and FEGRGYEASVDRLTF, respectively) were synthesized by Unimed Healthcare Inc. (Taipei, Taiwan). The N-terminal FITC-labeled peptide KY15 (FITC-KY15) was synthesized by Kelowna International Scientific Inc. (Taipei, Taiwan). Freund's adjuvants, keyhole limpet hemocyanin (KLH), glutaraldehyde, 3,3',5,5'-tetramethylbenzidine (TMB) liquid substrate, and FITC-insulin were purchased from Sigma-Aldrich (St. Louis, Mo., USA). Goat anti-rabbit IgG (H+L)-HRP was from Rockland Immunochemicals, Inc. (Gilbertsville, Pa., USA). Fluorescein-5-isothiocyanate cadaverine (FITC-cadaverine) was from AnaSpec, Inc. (San Jose, Calif., USA). BioMag magnetic dextran-coated charcoal (MD-Charcoal) concentrate (40 mg/ml, approximately 1.5 μm of particle size) was supplied by Bangs Laboratories, Inc. (Fishers, Ind., USA). MD-Charcoal concentrate was 5-fold diluted with water and stored at 4° C. for subsequent application. Ultrafiltration unit was from Millipore (Bedford, Mass., USA). V96 microplate (#249945) and ELISA strip (#469949) were from Nalge Nunc International (Rochester, N.Y., USA). Other chemicals used were analytical grade and from either Sigma-Aldrich, or Merck (Darmstadt, Germany), unless otherwise stated.

Production of Antisera

Peptides KY15 and FF15 were separately conjugated with KLH for rabbit immunization. The coupling reaction was performed by mixing each peptide with KLH (peptide: KLH=2:1, w/w) in 0.1 M borate buffer, pH 10.0, including 0.1% glutaraldehyde. After 1-hour incubation at room temperature, 1 M glycine was added to the mixture for another 1-hour incubation. The buffer of KLH-coupled peptides was changed to 0.1 M borate buffer, pH 8.5, by using a 30 K ultrafiltration unit (Amicon Ultra-4). KLH-coupled peptides mixed with equal volume of Freund's adjuvants were used to immunize rabbits (0.3 mg per rabbit) subcutaneously. The rabbits were boosted after two weeks of the primary injection, and the sera were collected 2 weeks later.

The Capturing Properties of MD-Charcoal for the FITC-Labeled Molecules

Aliquots of FITC-labeled molecules (3 μM in 60 μl) mixed with equal volume of reagent B (2 mM EDTA, 0.5 M Hepes-pH 8.0) were treated with MD-Charcoal (200 μl/well) at room temperature for 1, 5, or 10 minutes. MD-Charcoal was then magnetically precipitated, and then the fluorescent intensity in each well was directly read by a microplate reader (Plate Chameleon, Hidex Oy, Finland), without transferring supernatants to a new plate, with excitation wavelength set at 485 nm and emission wavelength at 535 nm (Ex485/Em535), at Gain 35.

Confirmation of Anti-KY15 Antiserum by ELISA

Peptide KY15 (5 μg/ml) dissolved in PBS buffer (137 mM NaCl, 2.7 mM KCl, 10 mM $Na_2HPO_4$, 2 mM $KH_2PO_4$, pH 7.4) was placed in ELISA plate wells (50 μl/well) and incubated at room temperature overnight. The residual binding capacity of the well was blocked with 5% skim milk (200 μl/well) at 37° C. for 30 minutes. After PBS wash, the anti-KY15 antiserum (diluted in skim milk, 1:500) was placed in the wells (50 μl/well), and the mixture was incubated at 37° C. for an hour. The wells were then washed with PBS buffer, and then the secondary antibody (goat anti-rabbit IgG (H+L)-HRP, diluted in skim milk (1:2500)) was added (50 μl/well). After incubation at 37° C. for one hour, the wells were rinsed again with PBS buffer. Finally, the chromogenic reaction was performed by adding TMB substrate solution (100 μl/well) and the result was monitored by absorbance at OD650. All experiments were performed in triplicates for each datum point and the data were presented as means±SD.

Detecting Anti-KY15 Antibody by Charcoal-Sorbent Peptide Binding Assay (CPBA)

Rabbit sera (30 μl/well) in microplate were 2-fold serially diluted in PBS buffer (137 mM NaCl, 2.7 mM KCl, 10 mM $Na_2HPO_4$, 2 mM $KH_2PO_4$, pH 7.4). After an aliquot of 30 μl of freshly prepared reagent-A (6 μM FITC-KY15, 100 mM Hepes-pH 7.5, and 2 mM EDTA) was added to each well, the microplate was incubated at 37° C. for 50 minutes. An aliquot of 60 μl of reagent B (0.5 M Hepes-pH 8.0, and 2 mM EDTA) was then added to each well to adjust pH to 8.0 for optimal fluorescence detection. To remove all the free fluorescent peptides, MD-Charcoal suspension (200 μl per well) was added, and the mixture was incubated at room temperature for 5 minutes. After MD-Charcoal was precipitated by magnet for 1 minute, the fluorescence intensity in each well was measured with microplate reader (Plate Chameleon, Hidex Oy, Finland) with excitation wavelength at 485 nm and emission wavelength at 535 nm (Ex485/Em535), Gain 35. Transfer of supernatants to a new plate for fluorescence counting was not necessary because the precipitated MD-Charcoal did not influence the measurement of fluorescence in supernatant (J. Biomol. Screen. 11 (7), 836-843). The binding capacity of antiserum for the fluorescent peptide probe was expressed as fluorescence intensity per well. All experiments were performed in triplicates for each datum point and the data were presented as means±SD.

Results

Figure 2:
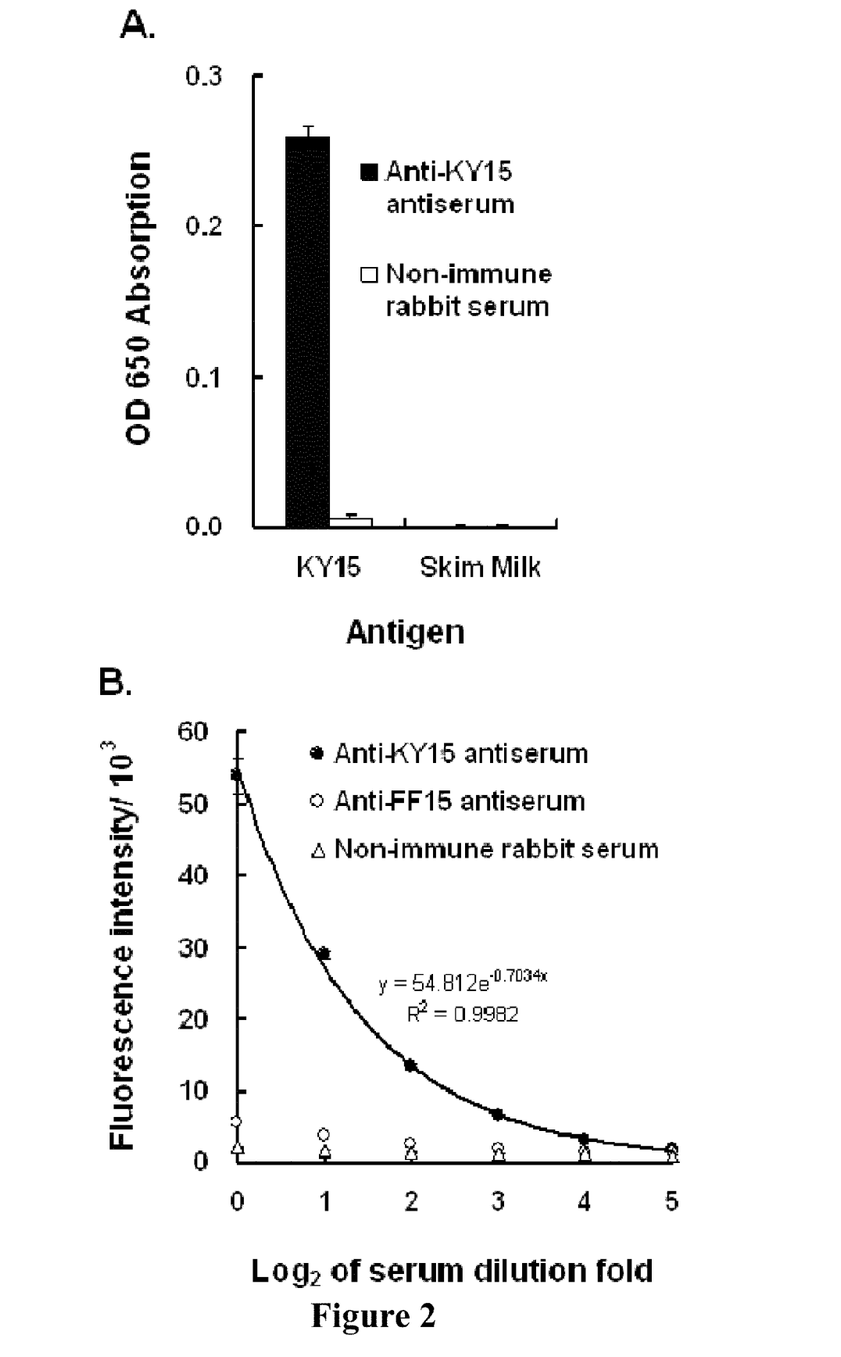
FIG. 2 illustrates the detection of anti-KY15 antibody.

The capturing rates of MD-Charcoal for FITC-labeled molecules are summarized in Table 1. The bulk (>99%) of FITC-labeled molecules was captured by MD-Charcoal within 5 minutes. This result indicates that small peptides can be rapidly removed by MD-Charcoal within a few minutes. As shown in FIG. 2A, the specificity of anti-KY15 antiserum for peptide KY15 is confirmed by ELISA. By using CPBA method for antibody detection (FIG. 2B), anti-KY15 antibody can be detected by the peptide probe, FITC-KY15. The result indicates that the method of the invention is superior to the ELISA method.

TABLE 1

Capturing capacity and rate of MD-Charcoal for FITC-labeled molecules

| MD-Charcoal treatment | FITC-labeled molecules | | |
|---|---|---|---|
| | FITC-cadaverine (MW 564) | FITC-KY15 (MW 2,334) | FITC-insulin (MW 6,123) |
| | Remaining fluorescence intensities | | |
| No Treatment | 328,801 ± 1,575[1a] (100.0%) | 215,345 ± 7,863[2a] (100.0%) | 366,310 ± 4,769[3a] (100.0%) |
| 1 min | 1,443 ± 68[1b] (0.4%) | 1,320 ± 410[2b] (0.6%) | 5,067 ± 356[3b] (1.4%) |
| 5 min | 1,130 ± 36[1b] (0.3%) | 1,037 ± 33[2b] (0.5%) | 2,550 ± 112[3b] (0.7%) |
| 10 min | 1,020 ± 37[1b] (0.3%) | 943 ± 29[2b] (0.4%) | 2,181 ± 115[3b] (0.6%) |
| Blank | 893 ± 9[1b] | 893 ± 9[2b] | 893 ± 9[3b] |

As shown in Table 1, aliquots of various FITC-labeled molecules (3 μM in 60 μl) were mixed with equal volume of reagent B (2 mM EDTA, 0.5 M Hepes-pH 8.0) in microplate wells separately, and then treated with/without MD-Charcoal (200 μl) for 1, 5, or 10 minutes. After MD-Charcoal was precipitated by magnet, the fluorescence of each well was measured at Ex485/Em535, Gain 35. Data were analyzed by one-way ANOVA and Tukey-HSD multiple range test, and presented as means±SD (n=3). Different successive superscript represents significant difference at p<0.05. The background value from empty well served as blank.

Example 2

Method for Detecting a Specific Antigen

Materials

The N-terminal FITC-labeled peptide RD18 and KY15 (amino acid sequences: RLIEDICLPRWGCLWEDD, and KSVGRDEREDITYTY, respectively) were synthesized by Kelowna International Scientific, Inc. (Taipei, Taiwan). Human serum albumin (HSA; #A3782; essentially fatty acid free, globulin free; 99% in purity) and ovalbumin (#A5503; from chicken egg white; 99% in purity) were purchased from Sigma-Aldrich (St. Louis, Mo., USA). Bovine gamma globulin (BGG; #A23212) was from Pierce Biotechnology (Rochford, Ill., USA). BioMag magnetic dextran-coated charcoal (MD-Charcoal) concentrate (40 mg/ml, approximately 1.5 µm of particle size) was supplied by Bangs Laboratories, Inc. (Fishers, Ind., USA). MD-Charcoal concentrate was 5-fold diluted with water and stored at 4° C. for subsequent application. V96 microplate (#249945) was from Nalge Nunc International (Rochester, N.Y., USA). Other chemicals used were analytical grade from either Sigma-Aldrich or Merck (Darmstadt, Germany) unless otherwise stated.

Detecting HSA by CPBA Method

The stock solutions of HSA, ovalbumin, and BGG were prepared as 125 µg/ml in HBS buffer (10 mM Hepes-pH 7.0, and 0.15 M NaCl). Aliquots of 30 µl of each protein placed in microplate wells were 2-fold serial diluted in HBS buffer. After an aliquot of 30 µl of freshly prepared reagent-A (6 µM FITC-RD18/FITC-KY15, 100 mM Hepes-pH 7.5, and 2 mM EDTA) was added to each well, the microplate was incubated at 37° C. for 30 minutes. An aliquot of 60 µl of reagent B (0.5 M Hepes-pH 8.0, and 2 mM EDTA) was then added to each well to adjust pH to 8.0 for optimal fluorescence detection. To remove all the free fluorescent peptides, MD-Charcoal suspension (200 µl per well) was added and incubated at room temperature for 5 minutes. After MD-Charcoal was precipitated by magnet for 1 minute, the fluorescence intensity in each well was measured by microplate reader (Plate Chameleon, Hidex Oy, Finland) with excitation wavelength at 485 nm and emission wavelength at 535 nm (Ex485/Em535), Gain 35. Transfer of supernatants to a new plate for fluorescence counting was not necessary because the precipitated MD-Charcoal did not influence the fluorescence in supernatant. Background level of fluorescence intensities was measured by replacing protein samples with HBS buffer. The binding capacities of antigens for the fluorescent peptide probes were expressed as net fluorescence intensity per well. All experiments were performed at least in triplicates for each datum point and the data were presented as means±SD.

Results

Figure 3:
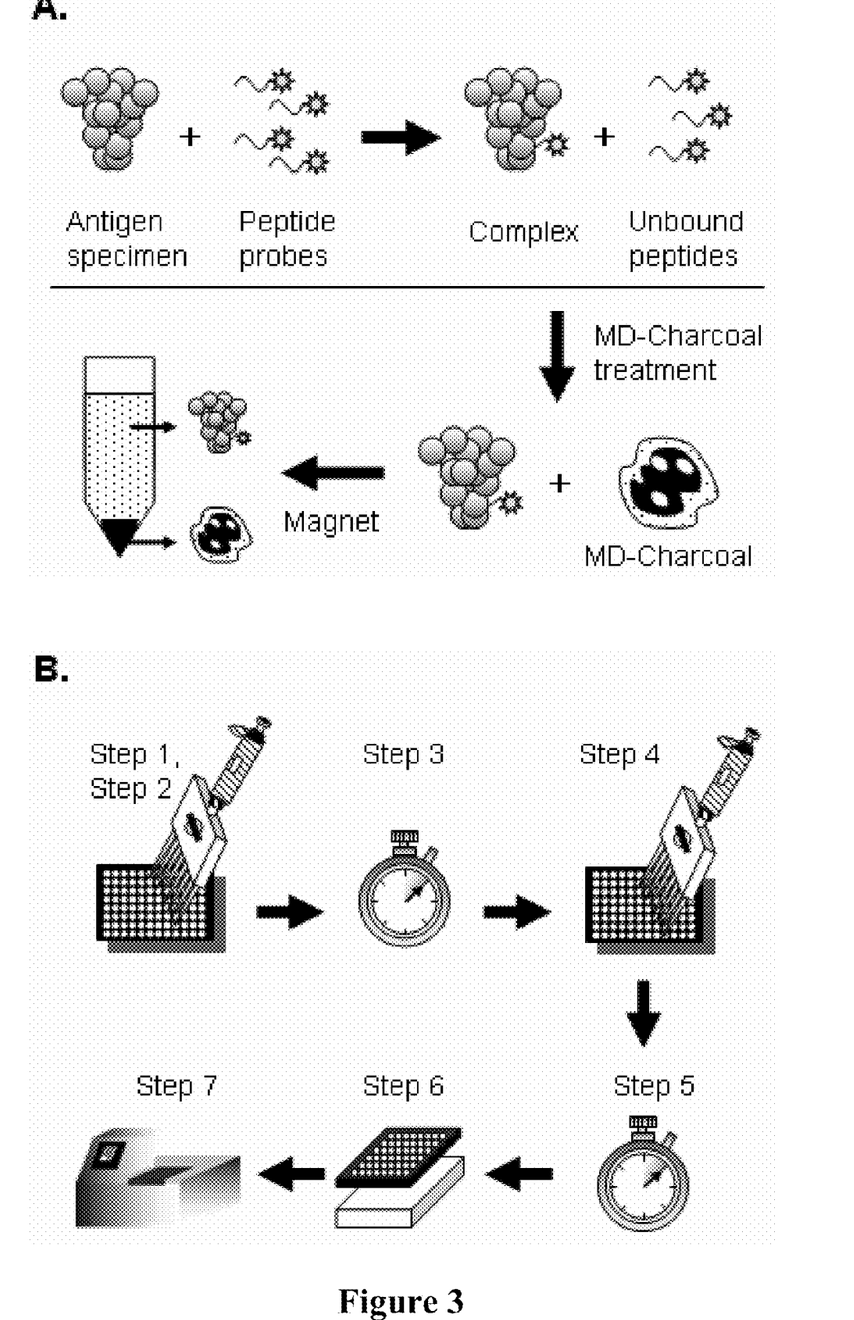
FIG. 3 illustrates the schemes of the antigen-detection method.
Figure 4:
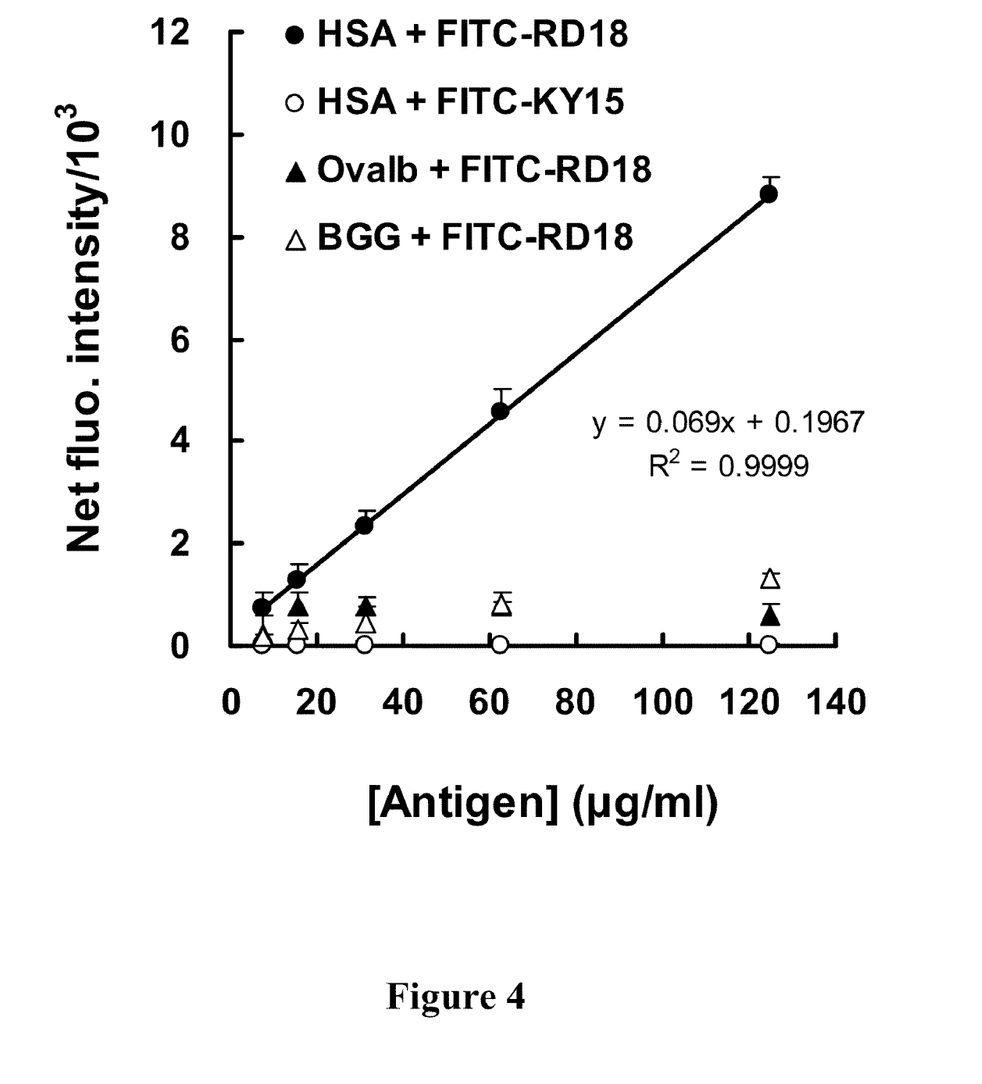

The binding specificity of albumin for FITC-RD18 is illustrated in FIG. 4. The controlled peptide, FITC-KY15, did not have affinity for albumin. RD18 was highly specific for albumin compared to control proteins, ovalbumin and bovine gamma globulin. The result indicates that the method of the invention illustrated in FIG. 3 is applicable and superior to other traditional analytical methods.

Example 3

Method for Detecting Multiple Antibodies and Antigens within a Specimen

Figure 5:
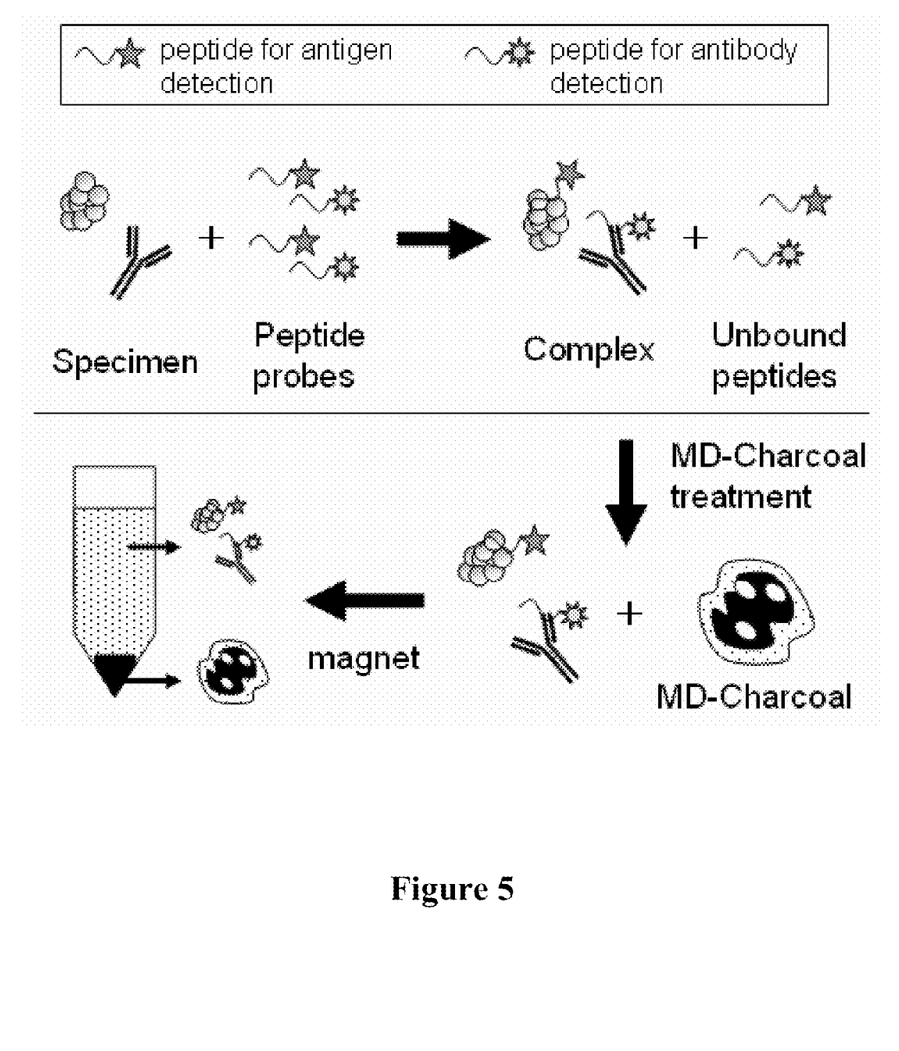

The technique can be applied to analyze multiple antibodies and antigens within one specimen. For this purpose, a mixture of distinct peptide probes is used to evaluate multiple antibodies and antigens within a specimen. Each probe has high affinity specifically for the respective target antibodies or antigens. Peptide probes used for different binding targets are labeled with distinguishable signal molecules such as fluorescent dyes or isotopes (e.g., $^3$H, $^{32}$P, $^{35}$S, $^{14}$C or $^{121}$I). After the incubation of peptide probes with the specimen, each binding complex is evaluated by detecting the various signal molecules. The assay scheme is illustrated in FIG. 5.

What is claimed is:

1. A high-throughput method for detecting at least two different target biomolecules in a sample, which comprises the steps of:
    (a) mixing at least two different fluorophore-labeled peptide probes with a specimen that contains said at least two different target biomolecules of respective probes, each said respective peptide probe only specifically binds to its respective said target biomolecule;
    (b) adding dextran-coated charcoal to the reaction mixture to capture all of the unbound fluorophore-labeled peptide probes, thereby adsorbing said unbound fluorophore-labeled peptide probes and causing said unbound fluorophore-labeled peptide probes to not exhibit fluorescent properties;
    (c) precipitating the dextran-coated charcoal by centrifugation or magnetic sedimentation so that unbound fluorophore-labeled peptide probes are separated from a supernatant; and
    (d) detecting the signals of the fluorophore in the supernatant with respective detection parameters while said unbound fluorophore-labeled peptide probes and said supernatant are still in a same container;
    wherein the at least two target biomolecules are large molecules that cannot be adsorbed by the dextran-coated charcoal and have a molecular weight of more than about 10 KD, and the respective probes are small molecules containing no more than 18 amino acids which can be adsorbed by the dextran-coated charcoal;
    and wherein after charcoal precipitation in step (c), it is unnecessary to transfer biomolecule-peptide probe complex to a new container for detection of fluorescence.

2. The method of claim 1, wherein the fluorophore is directly or indirectly labeled to the peptide probe.

3. The method of claim 1, wherein the fluorophore is the FITC, TRITC, rhodamine, or phycoerythrin.

4. The method of claim 1, wherein the target biomolecule is an antibody, an antigen, an enzyme, a pathogenic agent, a specific protein, a nucleic acid, a lipid, or a polysaccharide.

5. The method of claim 1, wherein the dextran-coated charcoal is a magnetic dextran-coated charcoal.

6. The method of claim 1, wherein the dextran-coated charcoal is precipitated by centrifugation.

7. The method of claim 5, wherein the magnetic dextran-coated charcoal is precipitated by a magnet.

8. The method of claim 1, wherein the biomolecule can be quantified by counting the signals of the marker.

9. A kit, for high-throughput detecting one or more target biomolecules in a sample, which comprises the fluorophore-labeled peptide probes and dextran-coated charcoal according to claim 1.

10. The kit of claim 9, which further includes packaging inserts setting out instructions for use.

* * * * *